(12) United States Patent
Bar-Tal et al.

(10) Patent No.: US 11,103,299 B2
(45) Date of Patent: Aug. 31, 2021

(54) ADAPTIVE ELECTRODE FOR BI-POLAR ABLATION

(71) Applicant: Biosense Webster (Israel) Ltd., Yokneam (IL)

(72) Inventors: Meir Bar-Tal, Haifa (IL); Yigal Ultchin, Rehovot (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 186 days.

(21) Appl. No.: 16/247,402

(22) Filed: Jan. 14, 2019

(65) Prior Publication Data

US 2019/0142500 A1    May 16, 2019

Related U.S. Application Data

(63) Continuation of application No. 13/971,887, filed on Aug. 21, 2013, now Pat. No. 10,213,248.

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1492* (2013.01); *A61B 18/1206* (2013.01); *A61B 2018/00107* (2013.01); *A61B 2018/00351* (2013.01); *A61B 2018/00577* (2013.01); *A61B 2018/124* (2013.01); *A61B 2018/1405* (2013.01); *A61B 2018/1435* (2013.01); *A61B 2018/1467* (2013.01); *A61B 2018/1497* (2013.01)

(58) Field of Classification Search
CPC . A61B 18/1206; A61B 18/14; A61B 18/1492; A61B 2018/00107; A61B 2018/00577; A61B 2018/124; A61B 2018/1405; A61B 2018/1435; A61B 2018/1467; A61B 2018/1497
USPC .................................................. 606/33-41
See application file for complete search history.

(56) References Cited

U.S. PATENT DOCUMENTS

| 5,680,860 A | 10/1997 | Imran |
| 5,823,955 A | 10/1998 | Kuck |
| 5,893,885 A | 4/1999 | Webster |
| 6,216,704 B1 | 4/2001 | Ingle |

(Continued)

FOREIGN PATENT DOCUMENTS

| CN | 102271607 | 12/2011 |
| JP | 2012-508083 | 4/2012 |
| JP | 2012-525933 | 10/2012 |

OTHER PUBLICATIONS

Examination Report for Australia Patent Application No. 2014213577, dated May 11, 2018.

(Continued)

*Primary Examiner* — Michael F Peffley
*Assistant Examiner* — Khadijeh A Vahdat
(74) *Attorney, Agent, or Firm* — Dergosits & Noah LLP; Todd A. Noah

(57) ABSTRACT

Cardiac ablation is carried out by placing two ablation electrodes on opposite sides of a wall of the heart to generally oppose one another. The effective current transmission area of one of the electrodes is then varied according to the distance between the two electrodes or the thickness of the wall. Sufficient electrical current is transmitted between the two electrodes to achieve transmural ablation.

15 Claims, 7 Drawing Sheets

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,319,250 B1 | 11/2001 | Falwell |
| 6,337,998 B1 | 1/2002 | Behl |
| 6,814,733 B2 | 11/2004 | Schwartz |
| 6,892,091 B1 | 5/2005 | Ben Haim |
| 6,997,924 B2 | 2/2006 | Schwartz |
| 7,156,816 B2 | 1/2007 | Schwartz |
| 7,497,858 B2 | 3/2009 | Chapelon |
| 7,536,218 B2 | 5/2009 | Govari |
| 7,756,576 B2 | 7/2010 | Levin |
| 8,114,069 B2 | 2/2012 | Levin |
| 8,177,780 B2 | 5/2012 | Cox |
| 2003/0045871 A1 | 3/2003 | Jain |
| 2003/0069572 A1 | 4/2003 | Wellman |
| 2004/0260273 A1 | 1/2004 | Wan |
| 2005/0149152 A1 | 7/2005 | Bertolero |
| 2005/0187545 A1 | 8/2005 | Hoovan |
| 2009/0124847 A1 | 5/2009 | Doty |
| 2010/0204560 A1 | 8/2010 | Salahieh |
| 2010/0286684 A1 | 11/2010 | Hata |
| 2012/0004560 A1 | 1/2012 | Sane |
| 2012/0071870 A1 | 3/2012 | Salahieh |
| 2012/0172872 A1 | 7/2012 | Nollert |
| 2012/0239021 A1 | 9/2012 | Doty |

OTHER PUBLICATIONS

Search Report and Office Action for China Patent Application No. 201404155849, dated Oct. 23, 2017.
European Search Report for European Patent Application No. 14181505.0; dated Oct. 23, 2014.
European Examination Report for European Patent Application No. 14181505.0; dated Dec. 1, 2015.
Search Report and Notification of Refusal for corresponding Japan Patent Application No. 2014-67382; dated Jun. 5, 2018.
Office Action for U.S. Appl. No. 13/971,887, dated Apr. 20, 2016.
Office Action for U.S. Appl. No. 13/971,887, dated Sep. 26, 2016.
Office Action for U.S. Appl. No. 13/971,887, dated Apr. 3, 2017.
Office Action for U.S. Appl. No. 13/971,887, dated Jul. 12, 2017.
Office Action for U.S. Appl. No. 13/971,887, dated Oct. 30, 2017.
Office Action for U.S. Appl. No. 13/971,887, dated May 31, 2018.

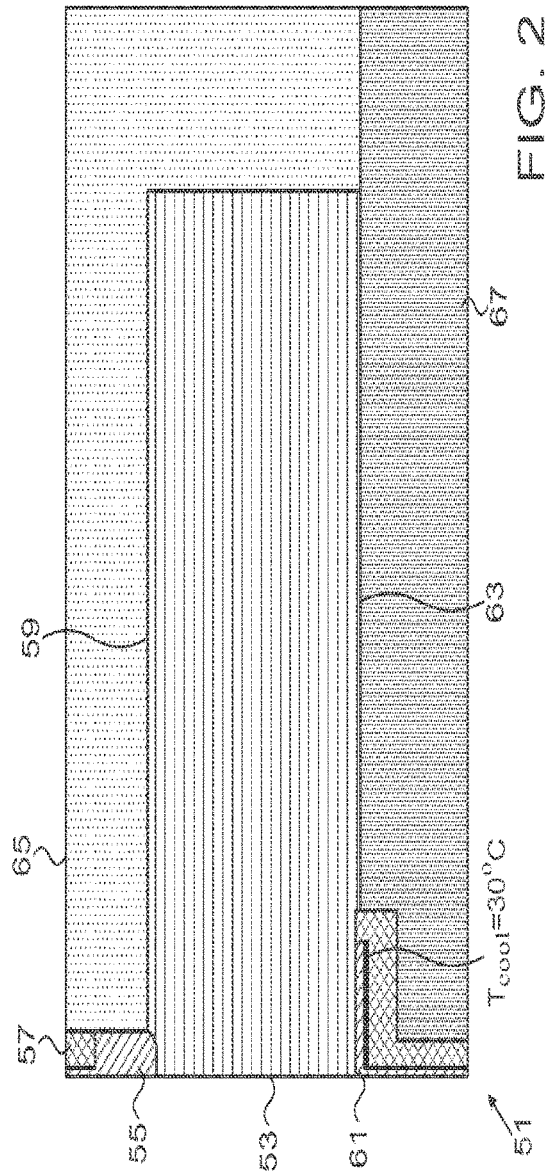
FIG. 2
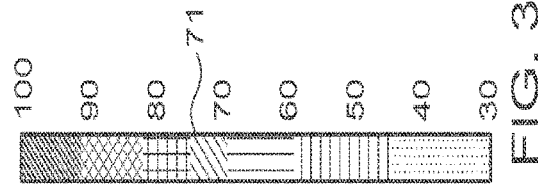
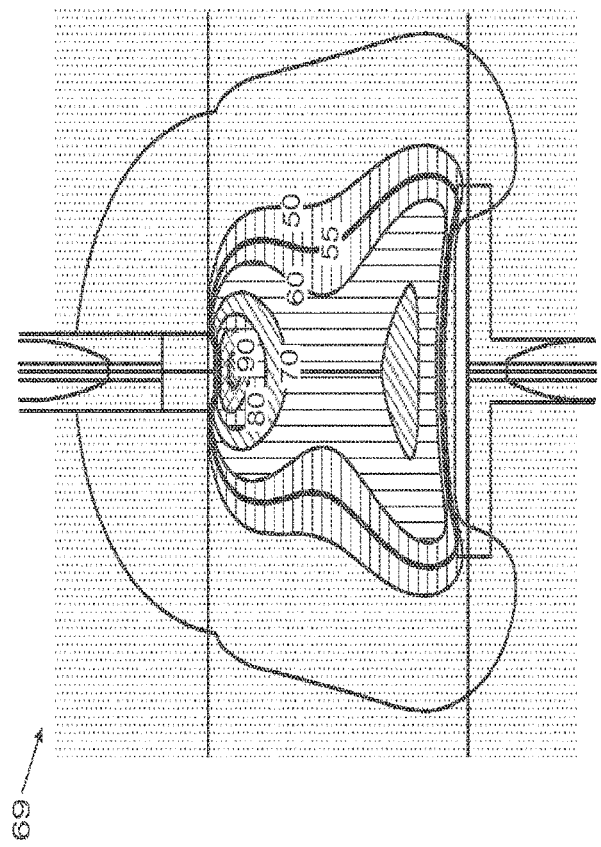
FIG. 3

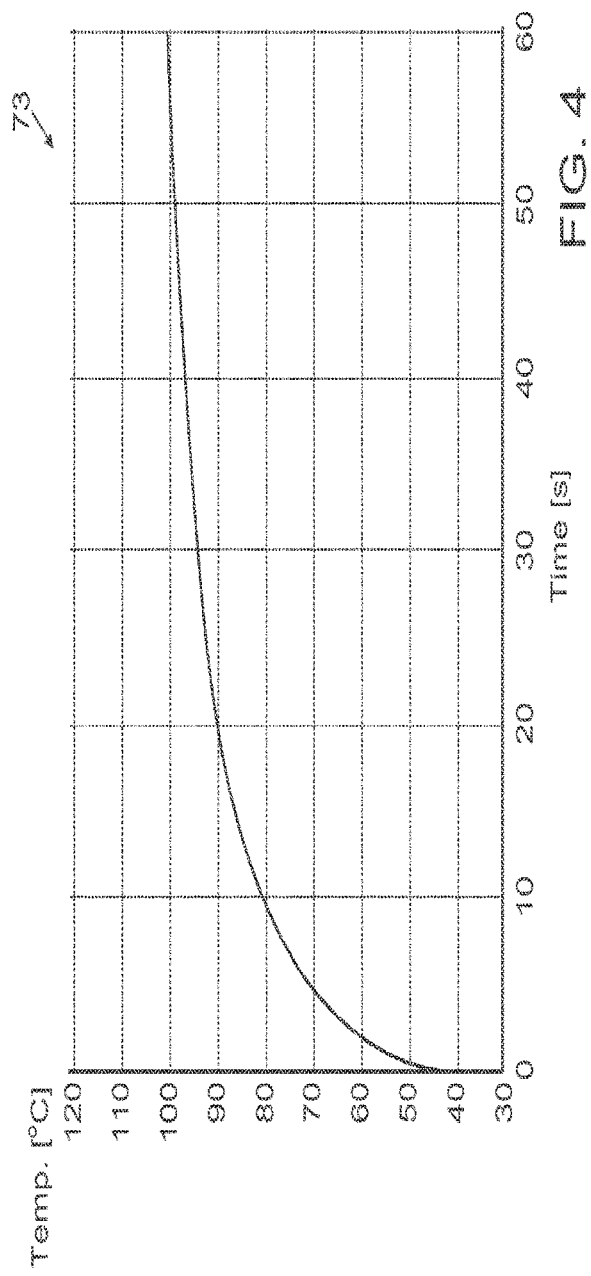
FIG. 4
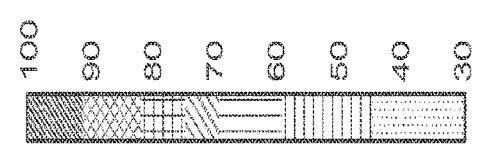
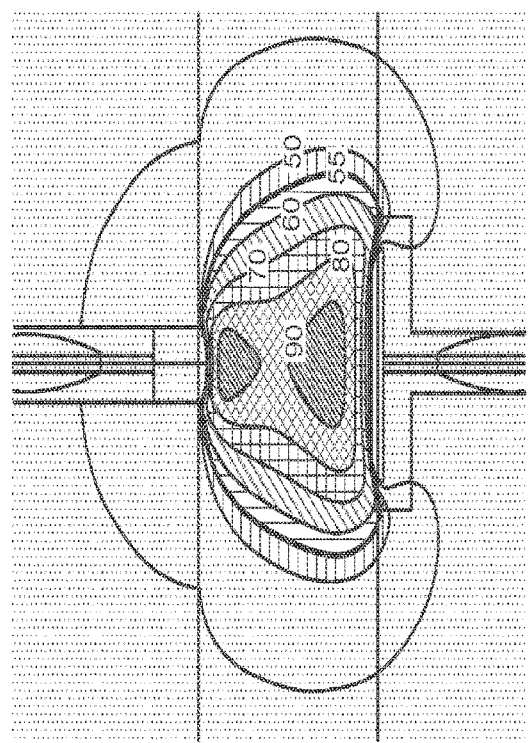
FIG. 5

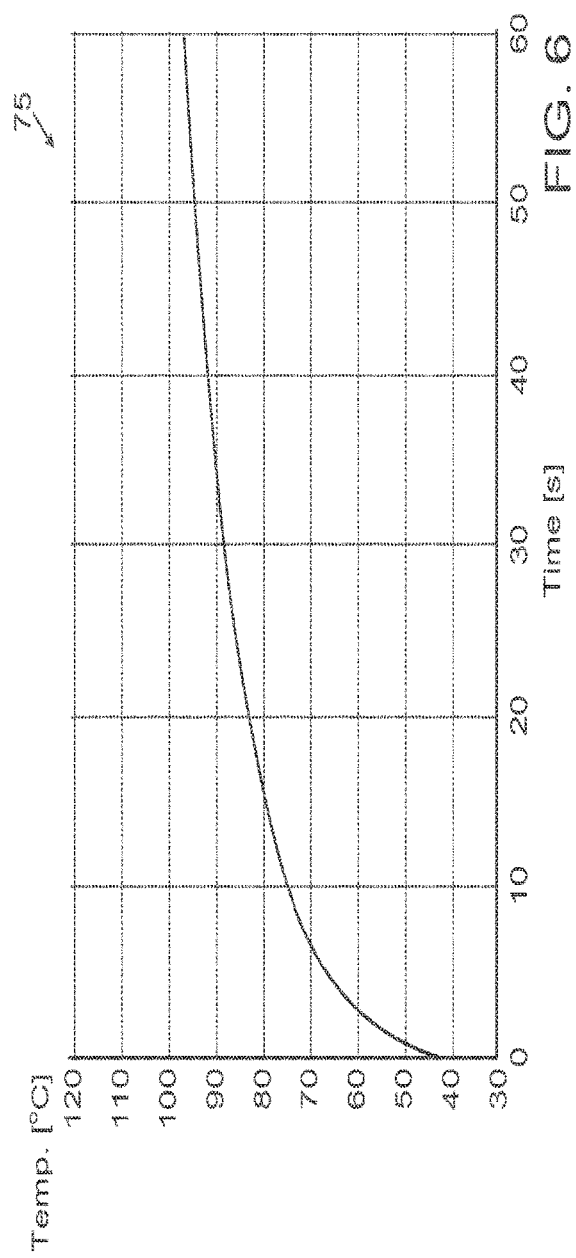
FIG. 6
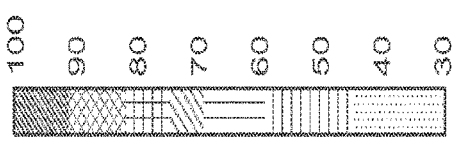
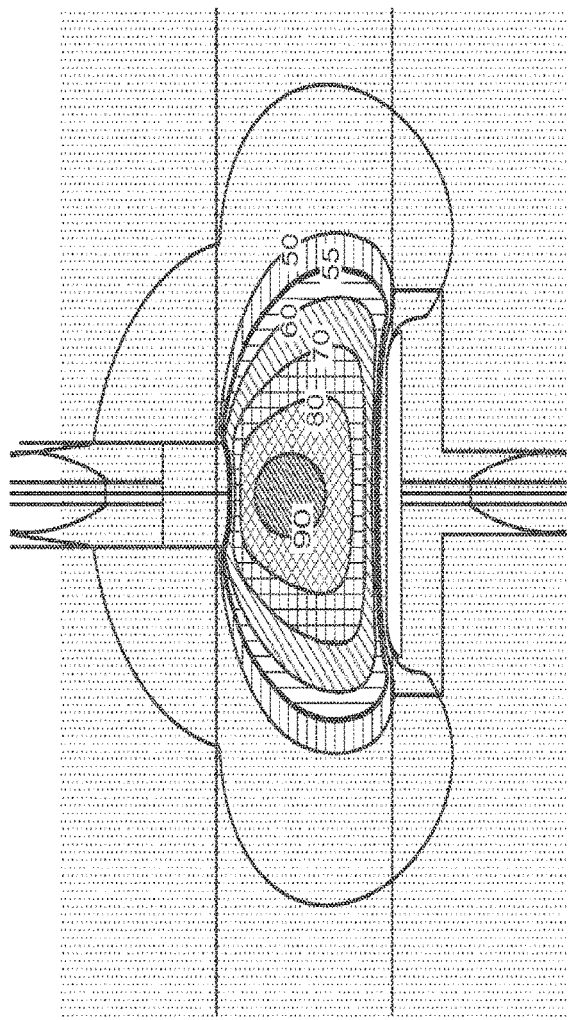
FIG. 7

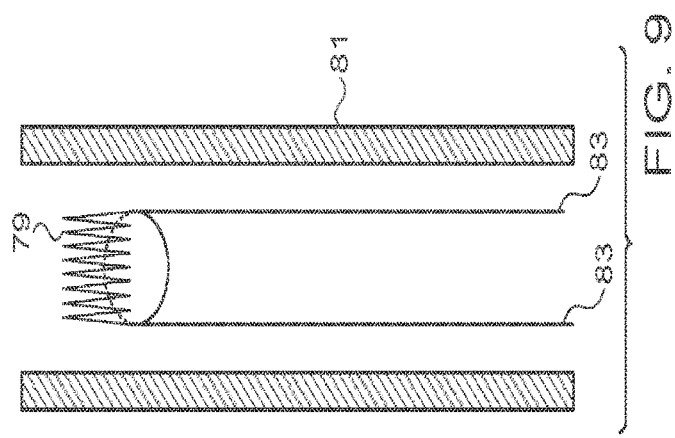
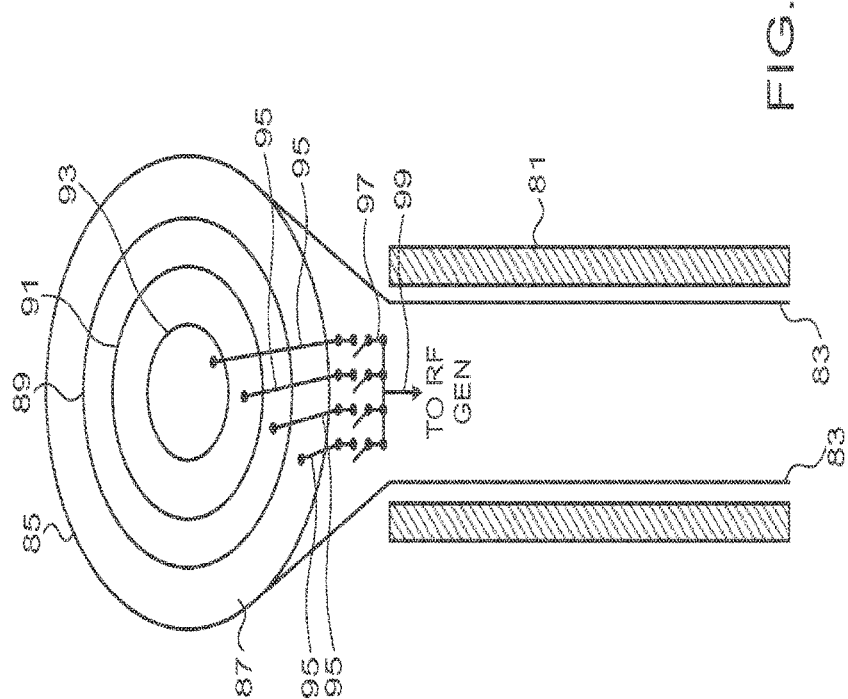

ADAPTIVE ELECTRODE FOR BI-POLAR ABLATION

CROSS-REFERENCE TO RELATED APPLICATIONS

This application is a continuation of commonly-assigned U.S. Patent Application Ser. No. 13/971,887, filed Aug. 21, 2013, now U.S. Pat. No. 10,213,248, the entire disclosure of which is incorporated by reference.

FIELD OF THE PRESENT DISCLOSURE

This invention relates to tissue ablation systems. More particularly, this invention relates to improvements in bipolar ablation.

DESCRIPTION OF THE RELATED ART

Cardiac arrhythmias, such as atrial fibrillation, occur when regions of cardiac tissue abnormally conduct electric signals to adjacent tissue, thereby disrupting the normal cardiac cycle and causing asynchronous rhythm.

Procedures for treating arrhythmia include surgically disrupting the origin of the signals causing the arrhythmia, as well as disrupting the conducting pathway for such signals. By selectively ablating cardiac tissue by application of energy via a catheter, it is sometimes possible to interrupt or modify the propagation of unwanted electrical signals from one portion of the heart to another. The ablation process destroys the unwanted electrical pathways by formation of non-conducting lesions.

The Maze procedure is one method of surgical treatment of atrial fibrillation. It involves making a series of incisions in the atria to construct a "maze" of scar tissue that acts as a barrier to the erratic electronic impulses associated with atrial fibrillation, allowing only those following the correct path to the heart to get through. Although highly successful, the Maze procedure is technically difficult and requires stopping the heart and placing the patient on a heart-lung machine.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

SUMMARY OF THE INVENTION

Bipolar radiofrequency ablation is one approach to simplifying the ablation procedure. Instead of using surgical incisions, doctors create a lesion in the heart by passing radiofrequency current through two electrodes located on opposite sides of the heart wall or septum, causing a transmural lesion 1-2 mm in width. The procedure does not require stopping the heart, and each lesion takes 9 seconds to complete, as opposed to 5-10 minutes per lesion using the Maze procedure.

Although transmural ablation in the left ventricle may be appropriate for treatment of arrhythmias such as refractory ventricular tachycardia, it is not feasible using current ablation catheters and methods. The effective ablation zone generated in the myocardium using an irrigated ablation catheter extends only about 5 mm beneath the contacting surface of the ablation electrode. As the left ventricle thickness may be at least 15 mm, it is apparent that even ablating from both sides of the ventricle fails to achieve the objective.

Embodiments of the present invention provide a catheter and method for adaptively shaping a lesion and effectively controlling its depth effectively to at least 15 mm.

There is provided according to embodiments of the invention a method of ablation, which is carried out by placing a first ablation electrode of a first probe at a first side of a wall of the heart of a living subject, placing a second ablation electrode of a second probe with at a second side of the wall to oppose the first ablation electrode, varying an effective current transmission area of the second ablation electrode, and flowing sufficient electrical current between the first ablation electrode and the effective current transmission area of the second ablation electrode to ablate the wall.

According to still another aspect of the method, flowing sufficient electrical current is performed while at least one of the first and second ablation electrodes is in contact with the wall.

According to another aspect of the method, flowing sufficient electrical current is performed while at least one of the first and second ablation electrodes is within 2 mm of the wall.

According to an additional aspect of the method, varying an effective current transmission area is performed responsively to the distance between the first and second ablation electrode.

According to one aspect of the method, varying an effective current transmission area is performed responsively to a thickness of the wall.

According to yet another aspect of the method, the second ablation electrode includes a plurality of segments, the segments is electrically insulated from one another, and each of the segments is switchably connectable to a source of the electrical current.

According to a further aspect of the method, the segments comprise concentric circles.

According to yet another aspect of the method, the segments are arranged in a spiral.

According to one aspect of the method, borders of the segments comprise triangles.

According to an additional aspect of the method, the triangles are similar triangles has a common geometric center.

According to still another aspect of the method, the effective current transmission area of the second ablation electrode is between 2 and 4 times as large as the effective current transmission area of the first ablation electrode.

According to yet another aspect of the method, the effective current transmission area of the second ablation electrode is between 3 and 4 times as large as the effective current transmission area of the first ablation electrode.

In another aspect of the method, the second ablation electrode comprises an electroconductive film and electrical signals are applied to the film to cause shape shifting thereof.

In yet another aspect of the method the second ablation electrode comprises an electroconductive film having a shape memory, and the method includes unfolding the film for deployment thereof and refolding the film for disengagement thereof with the subject.

According to an additional aspect of the method, the second ablation electrode is formed of a carbon-nanofiber, oxidized carbon-nanofiber, or carbon black-filled conductive shape-memory polyurethane composite.

There is further provided according to embodiments of the invention an ablation apparatus, including a first flexible probe adapted for insertion into the heart of a living subject and a first ablation electrode disposed at the distal segment of the probe, the probe adapted to be brought to a target tissue at a first side of a wall of the heart. The apparatus further includes a second ablation electrode adapted to be brought to a second side of the wall to oppose the first ablation electrode, the second ablation electrode including a plurality of segments that are electrically insulated from one another, and a power generator connectable to the first ablation electrode and switchably connectable to selected ones of the segments of the second ablation electrode for passing electric current between the first ablation electrode and the selected segments of the second ablation electrode.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 2 is a schematic diagram illustrating a simulation environment for evaluation of transmural ablation, in accordance with an embodiment of the invention;

FIG. 3 is a display of the temperature field in an experiment conducted using the simulation environment shown in FIG. 2, in accordance with an embodiment of the invention;

FIG. 4 is a graph indicating the relationship between the duration of current application and maximum temperature in the experiment illustrated in FIG. 3, in accordance with an embodiment of the invention;

FIG. 5 is a display of the temperature field in an experiment conducted using the simulation environment shown in FIG. 2, in accordance with an embodiment of the invention;

FIG. 6 is a graph indicating the relationship between the duration of current application and maximum temperature in the experiment illustrated in FIG. 5, in accordance with an alternate embodiment of the invention;

FIG. 7 is a display of the temperature field in an experiment conducted using the simulation environment shown in FIG. 2, in accordance with an alternate embodiment of the invention;

FIG. 9 is a schematic diagram of a patch electrode, shown retracted in a folded configuration within the lumen of an insertion tool, in accordance with an alternate embodiment of the invention;

FIG. 10 is a schematic diagram of a patch electrode, which has been extended beyond the insertion tool shown in FIG. 9 and unfolded for deployment in accordance with an embodiment of the invention.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as a diskette, hard drive, electronic media or CD-ROM. The code may be distributed on such media, or may be distributed to users from the memory or storage of one computer system over a network of some type to storage devices on other computer systems for use by users of such other systems.

Definitions

The term "effective current transmission area", when applied herein to an electrode, refers to an area of the electrode, which is operationally capable of supporting passage of an electric current through the electrode, e.g., between the electrode and a target to which the electrode is in contact.

System Description

Figure 1:
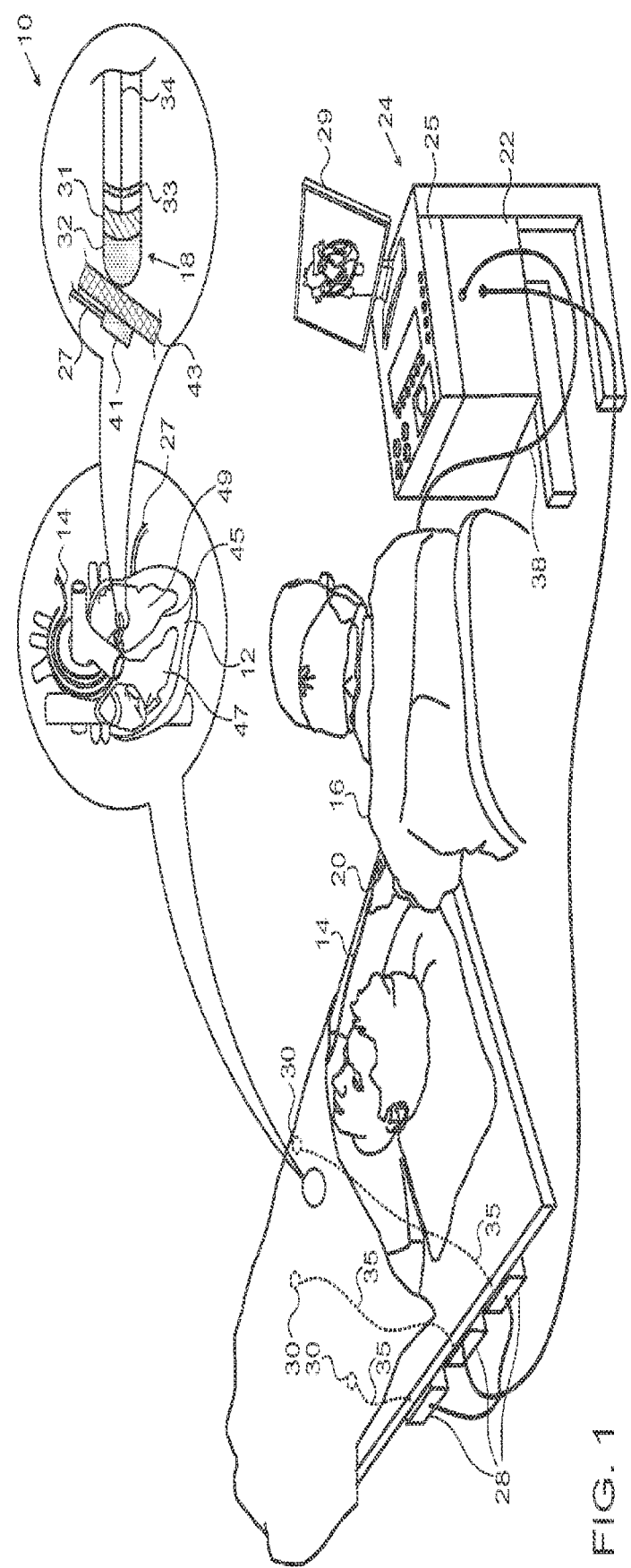
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with an embodiment of the invention. The system 10 comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Optionally, Electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at or near the distal tip 18, which apply the radiofrequency energy to the myocardium. The energy is absorbed in the tissue, heating it to a point (typically about 50.degree. C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, an ablation electrode 32 at or near its distal extremity, and having suitable controls on the handle to enable the operator 16 to steer, position and orient the distal portion of the catheter as desired for the ablation. To aid the operator 16, the distal portion of the catheter 14 contains position sensors (not shown) that provide signals to a positioning processor 22, located in a console 24.

A second probe, epicardial catheter 27 is connected to the console 24, and features an ablation element 41 at its working end. The ablation element 41 is positioned to oppose the ablation electrode 32 with target tissue 43 of the heart 12 therebetween. The ablation electrode 32 is connected via cable 34 to the console 24. The catheter 27 can be placed, for example, using the PerDUCER® Access Device, available from Comedicus Inc., 3989 Central Avenue N.E., Suite 610, Columbia Heights, Minn. 55421.

While the second probe is shown as an epicardial catheter in FIG. 1, this is not necessarily the case. For example, if it were required to ablate interventricular septum 45 the second probe would be introduced into the chamber of right ventricle 47 and the catheter 14 would contact the interventricular septum 45 from within the chamber of left ventricle 49 so as to oppose the second probe. The ablation element 41, shown schematically in FIG. 1, is described in further detail hereinbelow.

Ablation energy and electrical signals can be conveyed to and from the heart 12 through the ablation electrodes 32, 41. For example, pacing signals and other control signals may be conveyed from the console 24 through the cable 34 and the ablation electrode 32 to the heart 12. Sensing electrodes 31, 33, also connected to the console 24 are disposed near the ablation electrode 32 and have connections to the cable 34.

Wire connections 35 link the console 24 with body surface electrodes 30 and other components of a positioning sub-system. The ablation electrode 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near the ablation electrode 32.

The console 24 typically contains one or more ablation power generators 25. The catheters 14, 27 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheters 14, 27.

In one embodiment, the positioning subsystem comprises a magnetic position tracking arrangement that determines the position and orientation of the catheters 14, 27 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

As noted above, the catheters 14, 27 are coupled to the console 24, which enables the operator 16 to observe and regulate their functions. Console 24 includes a processor, preferably a computer with appropriate signal processing circuits. The processor is coupled to drive a monitor 29. The signal processing circuits typically receive, amplify, filter and digitize signals from the catheters 14, 27, including signals generated by the above-noted sensors and a plurality of location sensing electrodes (not shown) located distally in the catheters 14, 27. The digitized signals are received via cable 38 and used by the console 24 and the positioning system to compute the position and orientation of the catheters 14, 27 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheters 14, 27 for cooling the ablation site are provided.

Transmural Ablation

Reference is now made to FIG. 2, which is a schematic diagram illustrating a simulation environment 51 for evaluation of transmural ablation, in accordance with an embodiment of the invention. In the simulation, myocardium 53 has a tip electrode 55 of a conventional ablation catheter 57 applied to endocardium 59. An ablation patch 61, whose effective current transmission area is larger than that of the electrode 55, typically by a factor of between 2 and 4, and preferably 3 and 4 is applied to epicardium 63. The area 65 adjacent the endocardium 59 is simulates a thermally diffusive (.about.30 [W/m/K]) fluid 65. The epicardium 63 is simulated as bathed in fluid 67, which represents ordinary blood. The arrangement of FIG. 2 provides a simple temperature regulation mechanism in for the patch 61 that is equivalent to cooling using irrigation fluid to a temperature of 30.degree. C.

Example 1

Reference is now made to FIG. 3, which is a display of the temperature field in an experiment conducted using the simulation environment 51 (FIG. 2) in accordance with an embodiment of the invention. In this example, catheter diameter was 2.5 mm; the patch diameter was four times as large as the catheter diameter (4*2.5 mm); the RF current was 0.35 A; and the tissue thickness was 15 mm. The thermal gradient of heated zone 69 after 60 sec of ablation can be appreciated with reference to key 71. The 55.degree. C. isotherm is shown emphasized for convenience.

It should be noted that while tissue thickness was used in this and the following examples as the interelectrode distance, contact between the electrodes and the tissue is not essential. The techniques described herein are effective, even when there is a gap of about 2 mm between the electrodes and the tissue.

In this case ablation would occur within the 55.degree. C. isotherm. It is evident that this isotherm is transmural. As noted above, it is desirable to keeping the maximal temperature small enough to prevent steam-pops and charring.

Varying the patch diameter while holding the catheter electrode diameter constant controls the current density on both sides of the myocardium. The ratio of the patch diameter to the catheter diameter is adjusted to optimally shape the 55.degree. C. isotherm according to the actual myocardial thickness.

Too small a ratio will cause the peak temperature to rise too much on both sides. However, attempting to avoid this by lowering the current would result in with two smaller lesions that are not transmural. Increasing the diameter of the patch will lower the temperature at the patch and assure that the ablation is transmural.

Reference is now made to FIG. 4, which is a graph 73 similar to FIG. 3 indicating the relationship between the duration of current application and maximum temperature in the example of FIG. 3. A temperature of 80.degree. C. is achieved in about 10 seconds.

Example 2

Reference is now made to FIG. 5, which is another display of the temperature field in an experiment conducted using the simulation environment 51 (FIG. 2) after 60 sec of ablation using 0.3 Amp in accordance with an embodiment of the invention. In this example, the catheter diameter was 2.5 mm; the patch diameter was (3*2.5) mm; the current 0.3 A; and the tissue thickness 10 mm. When compared to FIG. 3, it is apparent from the 55.degree. C. isotherm that a wider, more uniform effective transmural ablation temperature has been achieved.

Reference is now made to FIG. 6, which is a graph 75 similar to FIG. 4, indicating the relationship between the duration of current application and maximum temperature. A temperature of 80.degree. C. is achieved in about 20 seconds, taking twice as much time as in the graph 73 (FIG. 4).

Example 3

Reference is now made to FIG. 7, which is another display of the temperature field in an experiment conducted using the simulation environment 51 (FIG. 2) in accordance with an embodiment of the invention. In this example, the catheter diameter was 2.5 mm; the patch diameter (3*2.5) mm; the current 0.25 A; and the tissue thickness 7 mm.

Figure 8:
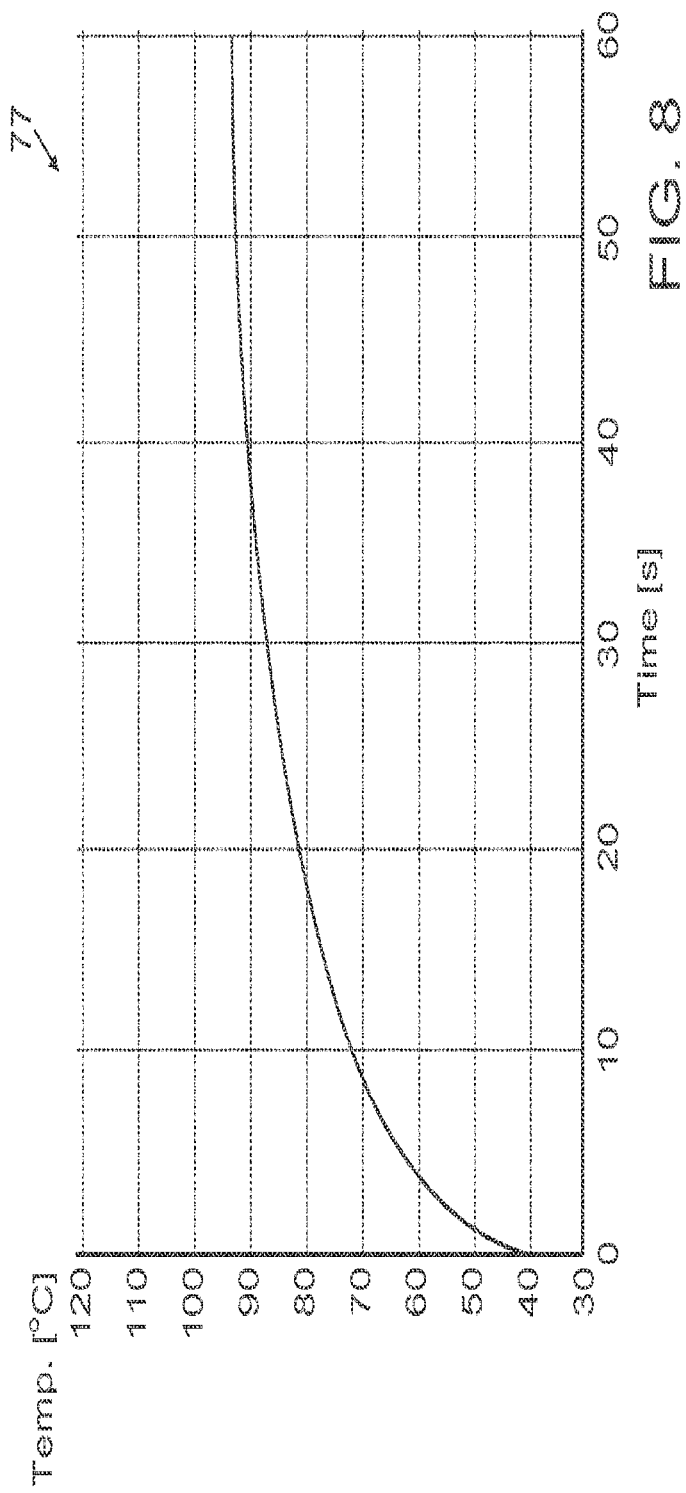
FIG. 8 is a graph indicating the relationship between the duration of current application and maximum temperature in the experiment illustrated in FIG. 7, in accordance with an alternate embodiment of the invention.

Reference is now made to FIG. 8, which is a graph 77 similar to FIG. 3, indicating the relationship between the duration of current application and maximum temperature in the example of FIG. 7.

Reference is now made to FIG. 9, which is a schematic diagram of a patch electrode 79, shown retracted in a folded configuration within the lumen of an insertion tool 81, in accordance with an embodiment of the invention. The electrode 79 can be advanced beyond the tool 81 using control wires 83, which may also serve to communicate radiofrequency current and electrical signals to and from the electrode 79.

The electrode 79 is composed of a thin electroconductive film or sheet that may have a shape memory, and is capable of shape shifting, optionally under control of electrical signals. In any case, the electrode 79 is able to unfold when extended during the medical procedure and to resume its folded configuration, so that it can be retracted into the lumen of the tool 81. For example, carbon-nanofiber, oxidized carbon-nanofiber, or carbon black-filled, conductive shape-memory polyurethane composites may be used to construct the electrode 79.

First Alternate Embodiment

Reference is now made to FIG. 10, which is a schematic diagram of a patch electrode 85, which has been extended beyond the tool 81 and unfolded for deployment in accordance with an embodiment of the invention. The electrode 85 is introduced via the tool 81 as described above with reference to FIG. 9. The electrode 85 is divided into a plurality of concentric circular segments 87, 89, 91, 93, which are electrically insulated from one another. Wires 95 lead from the segments 87, 89, 91, 93 to a series of switches 97, which can connect the segments individually or collectively to the console 24 and one of the ablation power generators 25 (FIG. 1) via a cable 99. Additionally or alternatively, the cable 99 may conduct electrical signals from the electrode 85 to the console 24 (FIG. 1) and control signals from the console 24 to the electrode 85. As different ones of the segments 87, 89, 91, 93 are switched in and out of electrical communication with the console 24, the effective current transmission area of the electrode 85 relating to the target tissue 43 (FIG. 1) may be varied according to requirements of the ablation procedure, as discussed above.

Second Alternate Embodiment

Figure 11:
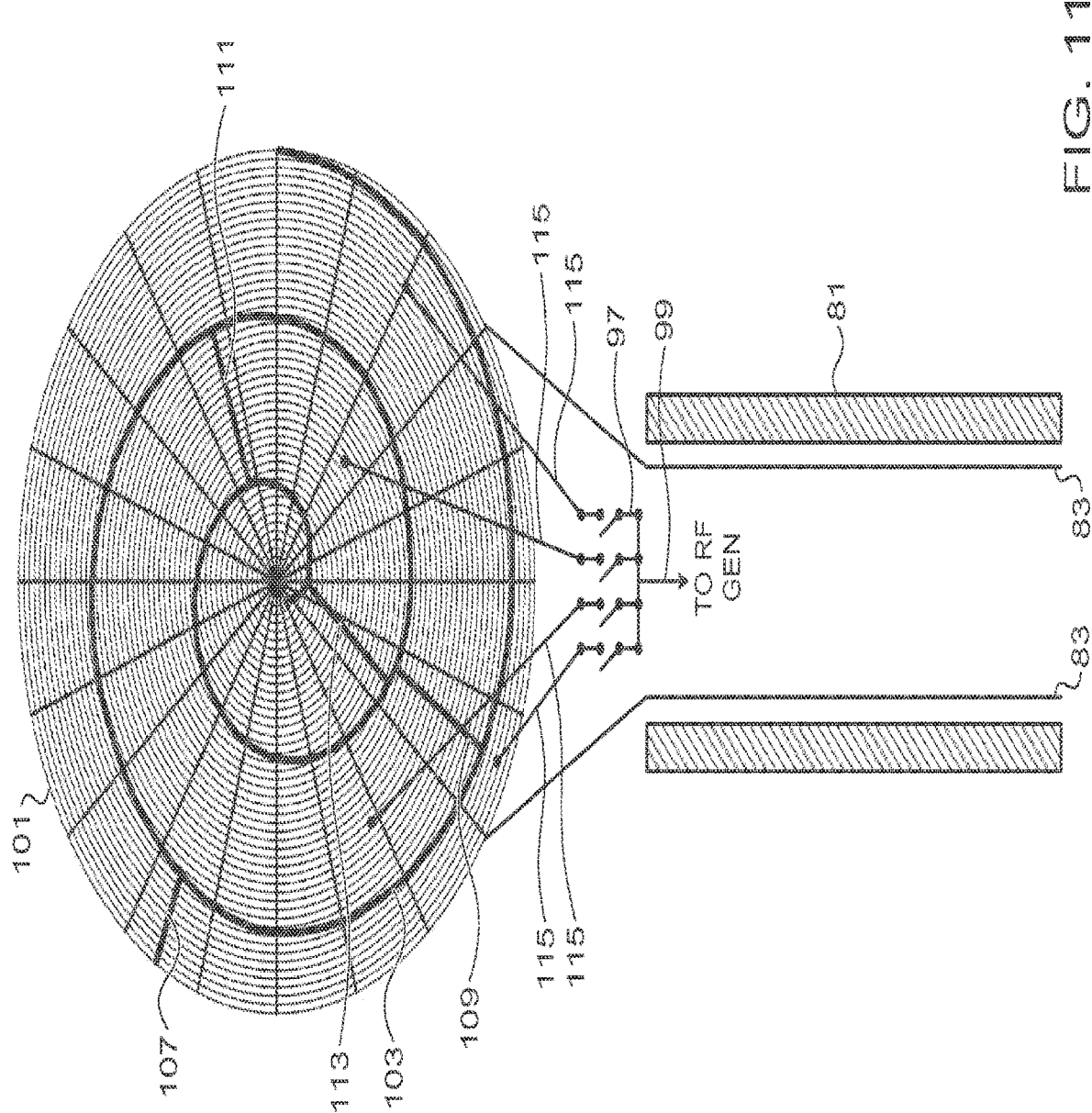
FIG. 11 is a schematic diagram of a patch electrode, which has been extended beyond the insertion tool shown in FIG. 9 and unfolded for deployment in accordance with an alternate embodiment of the invention.

Reference is now made to FIG. 11, which is a schematic diagram of a patch electrode 101, which is shown extended beyond the tool 81 and unfolded for deployment in accordance with an embodiment of the invention. The construction is generally similar to the embodiment of FIG. 10, however the sheet has a plurality of generally elongated, curved bands demarcated by a continuous insulation line 103 that follows a spiral course from a central point 105 outwardly toward the edge of the electrode 101. The bands are further segmented by transverse insulation lines 107, 109, 111, 113. The segments are attached to wires 115, which lead to the cable 99 via the switches 97.

While four segments are shown in the examples of FIG. 10 and FIG. 11, any number of segments may be provided to achieve a desired granularity in the size adjustment of the effective area of the electrodes 85, 101.

Other segmented geometric arrangements for a patch electrode are possible, for example a series of segments whose borders describe triangles, e.g., similar triangles having a common geometric center. It is only necessary that the effective current transmission area of the patch electrode exceed that of the opposing catheter electrode. In any case, appropriate selection of the segments optimizes the ratio between the effective current transmission area of the patch electrode and the catheter electrode.

Operation

Prior to a medical procedure, a database of optimum power settings and ratios of the effective current transmission areas of the electrodes is prepared for different inter-electrode distances, e.g., using the above-described simulation or experimentally using animal tissues.

When the electrodes are in position, the inter-electrode distance is determined, e.g., by the location sensing facilities of the CARTO system. The ablation settings may then be established automatically by switching in an appropriate number of segments of the patch electrode to create a desired ratio of the effective current transmission areas, and establishing an appropriate power output for the RF generator. Alternatively, the settings may be automatically determined and presented as recommendations to the operator who may approve or modify them.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

What is claimed is:

1. A method of ablation, comprising the steps of:
   placing a first ablation electrode of a first probe at a first side of a wall of a heart of a living subject;
   placing a second ablation electrode of a second probe at a second side of the wall to oppose the first ablation electrode;
   varying an effective current transmission area of the second ablation electrode; and
   flowing sufficient electrical current from the first ablation electrode and from the effective current transmission area of the second ablation electrode to transmurally ablate the wall.

2. The method according to claim 1, wherein flowing sufficient electrical current is performed while at least one of the first ablation electrode and the second ablation electrode are in contact with the wall.

3. The method according to claim 1, wherein flowing sufficient electrical current is performed while at least one of the first ablation electrode and the second ablation electrode are within 2 mm of the wall.

4. The method according to claim 1, wherein varying an effective current transmission area is performed responsively to a distance between the first ablation electrode and the second ablation electrode.

5. The method according to claim 1, wherein varying an effective current transmission area is performed responsively to a thickness of the wall.

6. The method according to claim 1, wherein the second ablation electrode comprises a plurality of segments, the segments being electrically insulated from one another, and each of the segments being switchably connectable to a source of the electrical current.

7. The method according to claim 6, wherein the segments comprise concentric circles.

8. The method according to claim 6, wherein the segments are arranged in a spiral.

9. The method according to claim 6, wherein borders of the segments comprise triangles.

10. The method according to claim 9, wherein the triangles are similar triangles having a common geometric center.

11. The method according to claim 1, wherein the effective current transmission area of the second ablation electrode is between 2 and 4 times as large as an effective current transmission area of the first ablation electrode.

12. The method according to claim 1, wherein the effective current transmission area of the second ablation electrode is between 3 and 4 times as large as an effective current transmission area of the first ablation electrode.

13. The method according to claim 1, wherein the second ablation electrode comprises an electroconductive film, further comprising the steps of applying electrical signals to the electroconductive film to cause shape shifting thereof.

14. The method according to claim 1, wherein the second ablation electrode comprises an electroconductive film having a shape memory, wherein placing the second ablation electrode further comprises the steps of unfolding the electroconductive film for deployment at the second side of the wall; and the method further comprising refolding the electroconductive film for disengagement of the second ablation electrode from the heart wall of the living subject.

15. The method according to claim 1, wherein the second ablation electrode comprises a carbon-nanofiber, oxidized carbon-nanofiber, or carbon black-filled conductive shape-memory polyurethane composite.

* * * * *